United States Patent [19]

Eikenberry et al.

[11] Patent Number: 4,782,018
[45] Date of Patent: Nov. 1, 1988

[54] DETECTION OF HYDROLYZING ENZYMES

[75] Inventors: Jon N. Eikenberry, Rochester; Karen L. Warren, Rush; Brooke P. Schlegel, Canandaigua; Dolores L. Humbert, Rochester, all of N.Y.

[73] Assignee: Eastman Kodak Company, Rochester, N.Y.

[21] Appl. No.: 819,667

[22] Filed: Jan. 17, 1986

[51] Int. Cl.$^4$ .................... C12Q 1/40; C12Q 1/34; C12Q 1/00; G01N 21/77
[52] U.S. Cl. .................................. 435/22; 435/4; 435/18; 436/169; 436/170; 436/807; 436/810
[58] Field of Search ............... 435/22, 4, 18; 436/169, 436/170, 810

[56] References Cited

U.S. PATENT DOCUMENTS 3,694,318  9/1972  Klein et al. ............... 195/103.5 R
4,144,306  3/1979  Figueras ........................ 422/56
4,478,944  10/1984  Gross et al. ................... 436/170
4,544,631  10/1985  Rauscher et al. ............... 435/14

OTHER PUBLICATIONS

Spayd, Richard W. et al., "Multilayer Film Elements for Clinical Analysis: Applications to Representative Chemical Determinations", *Clin. Chem.*, 24(8), 1343-1350, 1978.

Primary Examiner—Robert J. Warden
Assistant Examiner—Janelle Graeter
Attorney, Agent, or Firm—John R. Everett

[57] ABSTRACT

A composition of a polysaccharide with a detectable material appended thereto and a 1,3-dione having a methylene group between the two carbonyls of the 1,3-dione, which methylene group has at least one ionizable hydrogen, provides accurate results in assays of hydrolyzing enzymes such as amylase. The composition can be incorporated in the reagent zone of a dry test element having a reagent zone and a registration zone.

19 Claims, 4 Drawing Sheets

DETECTION OF HYDROLYZING ENZYMES

FIELD OF THE INVENTION

This invention relates to an improved composition and element for the detection and analysis of hydrolyzing enzymes in liquids, particularly the clinical analysis of amylase in biological liquids.

BACKGROUND OF THE INVENTION

Various techniques are used for the detection and analysis of hydrolyzing enzymes such as amylase. One useful technique is a wet chemistry assay technique involving a starch having a detectable material such as a colored or dye material attached thereto. Such an assay is described in U.S. Pat. No. 3,694,318. In that assay, a dyed starch (a starch having a preformed dye or dye former chemically attached) is dissolved or suspended in a liquid medium. The sample to be tested is then added to the liquid medium, whereupon the amylase present in the test sample hydrolyses the starch, causing release of the dye. The non-hydrolyzed starch is then removed separated and the amount of amylase present as a function of the amount of dye released is determined.

This dyed starch assay has been incorporated into dry test elements, as disclosed in U.S. Pat. No. 4,144,306. The element of that patent comprises: (i) a reagent layer containing a non-diffusible starch having attached thereto a detectable material such as a dye and (ii) a registration layer adapted to receive the detectable material. The sample of liquid to be tested is applied to the reagent layer, whereupon amylase in the sample hydrolyzes the starch, causing it to break down to low molecular weight polysaccharide units with the dye attached thereto. By virtue of their molecular weight, which is lower than that of the non-diffusible starch, the dye-containing low molecular weight polysaccharide units diffuse to the registration layer, where the amount of color formation and thus, the mount of amylase in the sample can be determined.

Dry test elements for the assay of hydrolyzing enzymes such as amylase, like the element described above, have been very successful because of their ease of use and because of fast and reliable results. However, when the test elements have been kept for a period of a week or more at ambient conditions, they have a tendency to overpredict the enzyme concentration as compared to freshly prepared elements or elements that have been stored under refrigeration. The present invention substantially alleviates the problem of overprediction of enzyme concentration in elements that have been stored at ambient conditions.

SUMMARY OF THE INVENTION

The problem of overprediction of enzyme concentration in polysaccharide-based assays using polysaccharides like dyed starch is substantially alleviated by using a composition comprising a polysaccharide having a detectable material appended thereto and a 1,3-dione having a methylene group between two carbonyls, which methylene group has at least one ionizable hydrogen.

A preferred class of 1,3-diones useful in the invention has the structure:

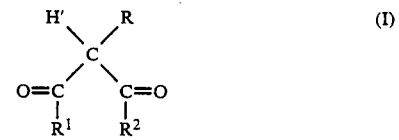

where H' is ionizable hydrogen, R is H, alkyl, aryl, or $-CO-R^3$, $R_1$ and $R^2$ each represent independently H, alkyl, aryl, $-OR^4$, a heterocyclic ring, or together represent the atoms necessary to complete a 5- or 6-membered carbocyclic ring, $R^3$ is H, alkyl, or aryl, and $R^4$ is alkyl or aryl.

The composition of the invention is advantageously incorporated in a dry test element. A particularly preferred test element comprises a reagent zone and a registration zone. This element comprises a non-diffusible polysaccharide and 1,3-dione as described above. Although the dione and polysaccharide can be in separate zones or layers in the element, it is preferred that they be combined in the reagent zone or layer. The reagent zone or layer can be considered a spreading zone or layer as well. The non-diffusible polysaccharide is interactive in the presence of the hydrolyzing enzyme being tested to provide a diffusible material comprising the detectable material that was appended to the nondiffusible polysaccharide. The registration zone of the element is adapted to receive this diffusible material.

DESCRIPTION OF THE DRAWINGS

FIG. 3 represents the tendency of elements outside the scope of the invention to overpredict enzyme concentration and FIG. 4 represents the reduced tendency of an element of the invention to overpredict enzyme concentration.

DESCRIPTION OF THE PREFERRED EMBODIMENTS

Figure 1:
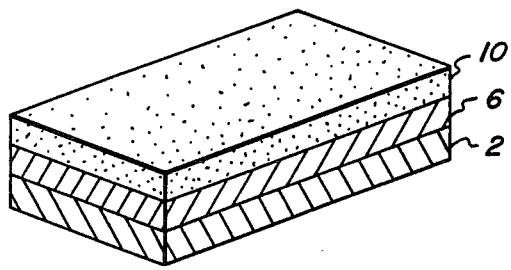
FIG. 1 shows an element according to the invention comprising a reagent layer and a registration layer on a support.

The polysaccharide of the invention is preferably a starch. Such starches are well-known in the art and can be obtained from a variety of sources, such as starch from potato, corn, tapioca, wheat, rice, sweet potato, or other sources. Both water-soluble and water-insoluble starches may be used. When used in the dry test elements of the invention, the polysaccharide should have a molecular weight sufficiently high to render it non-diffusible in that element.

The detectable material of the invention can be any number of well-known detectable materials, such as radioactive materials, and colored materials, such as chromogenic or fluorescent dyes. Useful detectable materials are described in U.S. Pat. No. 4,144,306, the disclosure of which is incorporated herein by reference in its entirety. Preferred materials are colored dyes, such as Drimarine Red Z2B sold by the Sandoz Corp.

of Hanover, NJ and various halogenated cyanuric dyes described in the above-referenced U.S. Pat. No. 4,144,306. The techniques for attaching the above-described detectable materials to polysaccharides such as starch are well-known in the art. Such techniques are disclosed in U.S. Pat. Nos. 3,579,322 and 3,694,318, the disclosures of which are incorporated herein by reference.

The composition of the invention also comprises a 1,3-dione as described above, having a methylene group between two carbonyls, which methylene group has at least one ionizable hydrogen. These 1,3-diones include beta-diketones, beta-ketoesters, beta-ketoaldehydes, and beta-dialdehydes. Examples of such 1,3-diones include:
dimedone (5,5-dimethyl-1,3-cyclohexanedione)
1-benzoylacetone
1-phenyl-2,4-pentaneadione 1-(2-furyl)-1,3-butanedione A preferred class of 1,3-diones useful in the invention has the structure:

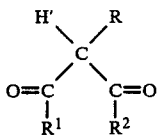

(I)

where H' is ionizable hydrogen, R is H, alkyl, aryl, or —CO—$R^3$, $R_1$ and $R^2$ each represent independently H, alkyl, aryl, —$OR^4$, a heterocyclic ring, or together represent the atoms necessary to complete a 5- or 6-membered carbocyclic ring, $R^3$ is H, alkyl, or aryl, and R is alkyl or aryl.

The hydrogen represented by H' is generally ionizable when the 1,3-dione has a $pK_a$ less than or equal to about 9. As is well known in the art, certain conditions, such as a high level of steric hindrance about H' or an easily hyrratable carbonyl adjacent to the H'-bearing carbon atom, can alter the ionizability of H'.

R, $R^1$, $R^2$, $R^3$, and $R^4$ can be any alkyl or aryl, substituted or unsubstituted, so long as the hydrogen represented by H' is ionizable. The alkyl group preferably has from 1 to 6 carbon atoms, such as methyl, ethyl, propyl, butyl, isopropyl, etc. Examples of useful aryl groups include phenyl, tolyl, methoxyphenyl, etc.

$R^1$ and $R^2$ can each be any substituted or unsubstituted heterocyclic group so long as the hydrogen represented by H' is ionizable. Preferred heterocyclic groups are those having 4 to 7 ring atoms, such as furyl, pyridyl, thienyl, pyrolyl, thiyl, etc.

$R^1$ and $R^2$ can also together represent the atoms required to complete a carbocyclic ring having 5 to 6 carbons in the nucleus. Exemplary carbocyclic rings include cyclopentane, cyclohexane, cyclopentene, cyclohexene, etc.

All the above-described groups represented by R, $R^1$, $R^2$, $R^3$, and $R^4$ may be unsubstituted or substituted with groups, such as alkyl (e.g., methyl, ethyl, butyl, hexyl, etc.); aryl, (e.g., phenyl tolyl, methoxyphenyl, hexadecyloxyphenyl, naphthyl etc.); cyano; and carbalkoxy (e.g. carbomethoxy, carboethoxy, carbobutoxy, etc.), etc., so long as the hydrogen represented by H' is ionizable.

An especially preferred class of 1,3-diones useful in the invention are carbocyclic 1,3-diones represented by the structure:

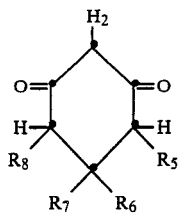

(II)

wherein $R_5$ and $R_8$ each represent a group selected from the class consisting of hydrogen; alkyl (e.g., methyl, ethyl, butyl, etc.); aryl (e.g., phenyl, tolyl, naphthyl, etc.); cyano; and carbalkoxy (e.g., carbomethoxy, carboethoxy, etc.); and $R_6$ and $R_7$ are each selected from the class consisting of hydrogen, alkyl (e.g., methyl, ethyl, butyl, amyl, etc.); and aryl (e.g., phenyl, methoxyphenyl ethoxyphenylhexadecyloxyphenyl, tolyl, naphthyl, etc.).

Examples of carbocyclic 1,3-diones useful in the present invention include:
(1) 5,5-dimethylcyclohexane-1,3-dione
(2) 5-phenylcyclohexane-1,3-dione
(3) 5-(p-methoxyphenyl)cyclohexane-1,3-dione
(4) 4-cyano-5-phenylcyclohexane-1,3-dione
(5) 5-(o-decyloxyphenyl)cyclohexane-1,3-dione
(6) 5-(o-hexadecyloxyphenyl)cyclohexane-1,3-dione
(7) cyclohexane-1,3-dione
(8) 4,6-dicarbethoxy-5-methylcyclohexane-1,3-dione
(9) 4,6-dimethyl-5-phenylcyclohexane-1,3-dione
(10) 4,6-dicyano-5,5-dimethylcyclohexane-1,3-dione
(11) 4-phenyl-5,5-diethylcyclohexane-1,3-dione
(12) 5-methyl-5-phenylcyclohexane-1,3-dione
(13) cyclopentene-1,3-dione
(14) 4,4-dimethylcyclopentane-1,3-dione.

Further description of carbocyclic 1,3-diones, including their preparation, is found in U.S. Pat. No. 3,447,926, the disclosure of which is incorporated herein by reference.

In the composition of the invention, the polysaccharide having the detectable material attached thereto and the 1,3-dione can be combined in any ratio which provides the invention's advantageous reduction in overprediction of enzyme concentration. Since even a small amount of 1,3-dione will produce some effect, compositions having such small amounts are within the scope of the invention. The specific desirable concentrations depend on the particular polysaccharide and 1,3-dione utilized and can be easily determined by testing the composition with samples having known enzyme concentrations. Preferred concentrations of 1,3-dione range from 1 to 40 parts by weight of dione per 100 parts by weight of polysaccharide. A particularly preferred 1,3-dione of the present invention is dimedone (i.e., 5,5-dimethyl-1,3-cyclohexanedione). A preferred concentration of dimedone ranges from 2 to 20 parts by weight of dimedone to 100 parts by weight of polysaccharide.

In a preferred embodiment of the invention, the composition also comprises a binder, an inert particulate material, and a buffer in addition to the above-described polysaccharide and 1,3-dione. The binder can be any of the reagent carriers disclosed in the above-referenced U.S. Pat. No. 4,144,306, but a particularly preferred class of binders are isotropically porous polymers such as blushed polymers. Blushed polymers can be formed on a substrate by dissolving a polymer in a mixture of two liquids, one of which is a lower boiling, good solvent for the polymer and the other of which has a higher boiling point and is a non-solvent or a poor solvent for the polymer. Such a polymer solution is then coated on the substrate, and dried under controlled conditions. The lower-boiling solvent evaporates more readily and the coating can become enriched in the liquid which is a poor solvent or non-solvent. As evaporation proceeds, under proper conditions, the polymer forms as an isotropically porous layer. Many different polymers can be used, singly or in combination, for preparing isotropically porous blushed polymer layers for use in this invention, for example, polycarbonates, polyamides, polyurethanes and cellulose esters such as cellulose acetate. Various microporous filters are, or are partly, blushed polymeric compositions, for example, various membrane filters of the Millipore Corporation, and they have been described in patents such as U.S. Pat. Nos. 2,783,894 and 2,772,322. The porosity of the blushed polymer should be such that the non-diffusible polysaccharide of the invention will not diffuse through it, but the diffusible material will.

The inert particulate material of the invention can be any material such as pigments, diatomaceous earth, or microcrystalline colloidal materials, such as microcrystalline cellulose. Particularly preferred inert particle materials are light reflective pigments, such as barium sulfate, titanium dioxide, zinc oxide, and lead oxide. Particle size should be chosen to be compatible with the porosity of the blushed polymer. The amount of pigment to be included in the composition varies greatly and is generally between 5 and 2000 percent based on the weight of the binder.

It is preferable in the dyed starch assay of hydrolyzing enzymes such as amylase to utilize a buffer for maintaining the pH in the appropriate range. Preferred buffers are those that maintain the pH in the range of 6 to 8. Such buffers include triethanolamine and sodium dihydrogen phosphate. Other suitable buffers are well-known in the art. A partial listing of specific representative buffer compositions is given by Good in *Biochemistry*, 5, p. 467 (1966).

Figure 2:
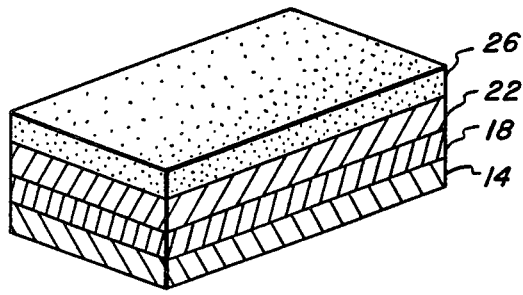
FIG. 2 shows an element according to the invention comprising a reagent layer, a buffer layer, and a registration layer on a support.

The test element of the invention comprises one or more reagent zones and registration zones. In one embodiment of the invention, the element also comprises one or more buffer zones between the reagent zone(s) and the registration zone(s). The elements may be self-supporting, but are preferably on a support. Referring to the drawings, FIG. 1 represents a test element of the invention having a support 2, a registration layer 6, and a reagent layer 10. FIG. 2 represents a test element of the invention having a support 14, a registration layer 18 a buffer layer 22, and a reagent layer 26.

Reagent zones of the invention comprise the above-described polysaccharide and 1,3-dione and is preferably permeable and porous. Permeability, incuding permeability arising from porosity, can be achieved through the presence of various carriers, matrices, or binders, such as fibrous materials or porous, non-fibrous materials described in the above-referenced U.S. Pat. No. 4,144,306. A preferred permeable binder of the invention is the abovedescribed class of blushed polymers. Also useful as a porous carrier is a polymer binder with an inert particulate material, such as microcrystalline cellulose, dispersed therein. Pigment particles may be incorporated in the reagent zone for light reflecting purposes.

Registration zones according to the present invention are described in the above-referenced U.S. Pat. No. 4,144,306. The registration zone is permeable to the detectable material-containing diffusible material and is preferably radiation-transmissive to allow detection of the detectable material. The registration zone is adapted to receive the diffusible material from the reagent zone. When the diffusible material comprises a detectable material that is a dye, the registration zone may contain a mordant for that dye. Such mordants are well-known in the photographic arts. Particularly useful mordants are polymeric mordants having repeating units of the formula:

wherein A represents an organo group, such as an alkylene group, forming a portion of the polymer backbone, Q represents a chemical bond or an organo group linking $M^+$ to A, $M^+$ represents a quaternary ammonium or phosphonium group, and $X^-$ represents an anion. Such mordants are described in U.S. Pat. No. 4,069,017, the disclosure of which is incorporated herein by reference in its entirety.

The elements of the present invention may include other zones well-known in the clinical analysis art. These other zones include spreading zones, radiation blocking zones including reflecting zones, filter zones, subbing layers, and the like. The composition of these zones and their location in the element are known in the art and are described in U.S. Pat. No. 3,992,158, and the above referenced U.S. Pat. No. 4,144,306, which are incorporated herein by reference. For example, spreading zones can be isotropically porous zones, achieving such porosity through the use of inert particle materials and/or blush polymers, and can be positioned adjacent to the reagent zone as the outermost layer of the element (if a multilayer element is used). Reflecting zones can include pigments such as titanium dioxide, barium sulfate, and the like and/or blushed polymers, which are generally reflective in nature. Reflecting zones may be positioned between the reagent zone and the registration zone or the spreading zone. Filter zones, which may be the same as or different from the reflecting zone, may also include inert particulate materials and/or blushed polymers and may be positioned between the reagent zone and the registration zone or the spreading zone. Subbing layers are well-known in the clinical analysis and photographic arts and may be positioned anywhere in the element. Any of the zones of the present invention may also include well-known addenda, such as buffers, surfactants, or coating aids, as described in the above-referenced U.S. Pat. No. 4,144,306.

Multilayer elements of the invention can be prepared by various laminating or coating techniques well-known in the art, such as hand-coating, blade coating, bead coating, or dip coating. The elements may be self-supporting or carried on a support. Useful support materials include a variety of polymeric materials, such as cellulose acetate, poly(ethyleneterephthalate), polycarbonates, and polyvinyl compounds such as polystyrenes. The support should be chosen so that the presence of the detectable material may be detected through the support. For example, if the detectable material is a colored dye, the support is preferably transparent to light. Coating and laminating techniques, along with support materials, are further described in the above-referenced U.S. Pat. No. 4,144,306.

For coatable reagent zones, a coating solution or dispersion including a binder and the polysaccharide can be prepared, coated as discussed herein and dried to form a dimensionally stable zone. The thickness of any reagent zone and its degree of permeability are widely variable and depend on actual usage. Dry thicknesses of from about 10 microns to about 100 microns are convenient, although more widely varying thicknesses can be used. For example, if comparatively large amounts of polysaccharide are required, it may be desirable to use slightly thicker reagent zones. Fibrous reagent zones can be formed by impregnation of a fibrous matrix, in accordance with well-known techniques.

Registration zones and other zones can be prepared using methods and thicknesses as used when preparing coatable reagent zones, but with constituents appropriate for the particular zone.

The elements of the invention are used by applying a sample of the liquid to be tested to the element. Generally, the element will be formed so that the liquid first contacts one or more spreading zones, if present, or the reagent zone(s). After application of the liquid, the element may be exposed to any conditioning, such as heating or humidification, that is desirable to quicken or otherwise facilitate any test result. After an appropriate time to allow for diffusion from the reagent zone to the registration zone of any detectable materialcontaining diffusible material released from the polysaccharide, the amount of detectable material in the registration zone is determined. Such a determination may be made by passing the element through an area in which an apparatus suitable for reflection, transmission, or fluorescence spectrophotometry is provided. Such apparatus serves to direct a beam of energy, such as light, through the support and the registration zone or the reagent zone. The light is then be reflected, such as from the reagent zone or a reflection zone in the element, back to a detecting means or passes through the element to a detector, in the case of transmission detection. Use of reflection spectrophotometry can be advantageous in some situations as it can effectively avoid interference from residues, such as blood cells, which may be left on or in the zones of the element. Conventional techniques of fluorescence spectrophotometry can also be employed if the detectable species is a fluorescent material. Detection would be accomplished using energy that excites the fluorescent species and a detector that senses its fluorescent emission. Furthermore, when blood serum is tested or means are provided for eliminating unwanted whole blood residues, transmission techniques can be used to detect and quantify the indicating reaction products by directing a flow of radiant energy, for example, U.V., visible, or I.R. radiation at one surface of the element and measuring the output of that energy from the opposing surface of the element. Generally, electromagnetic radiation in the range of from about 200 to about 900 nm has been found useful for such measurements, although any radiation to which the element is permeable and which is capable of quantifying the product produced in the element can be used. Various calibration techniques can be used to provide a control for the analysis. As one example, a sample of a standard test liquid can be applied adjacent to the area where the drop of sample is placed in order to permit the use of differential measurements in the analysis.

The following examples further illustrate the present invention:

EXAMPLE 1

An element for the assay of amylase according to the invention is prepared having the configuration shown in FIG. 2 on a poly(ethylene terephthalate) support. Additionally, the element has a subbing layer of polyvinylpyrrolidone coated at 0.540 g/m² between the reagent layer and the registration layer. The reagent layer is coated with the following coverages:

| | |
|---|---|
| BaSO$_4$ particles | 83.6 g/m² |
| Blushed cellulose acetate (40% acetylated) | 6.7 g/m² |
| Polyurethane elastomer, Estane Resin 5715 (sold by B. F. Goodrich) | 1.3 g/m² |
| Triton X-405 surfactant (sold by Rohm and Haas) | 2.5 g/m² |
| Dyed starch (Amylopectin sold by National Starch and Chemical Corp. of Buffalo, N.Y. and Drimarine Red Z2b sold by Sandoz Corp. of Hanover, N.J.) | 2.5 g/m² |
| Dimedone | 0.1 g/m² |

The buffer layer is coated with the following coverages:

| | |
|---|---|
| gelatin | 2.7 g/m² |
| Triton X-405 surfactant | 0.1 g/m² |
| Triethanolamine | 2.1 g/m² |
| H$_3$PO$_4$ | 0.7 g/m² |

The registration layer is coated with the following coverages:

| | |
|---|---|
| gelatin | 1.9 g/m² |
| Triton-X-405 surfactant | 0.1 g/m² |
| poly(styrene-co-N—vinylbenzyl-N,N—dimethyl-benzylammonium chloride-co-divinylbenzene) | 0.9 g/m² |
| NaH$_2$PO$_4$ | 0.2 g/m² |

For comparison, an element is prepared identically to the above-described element, except that no dimedone is present in the reagent layer.

Figure 3:
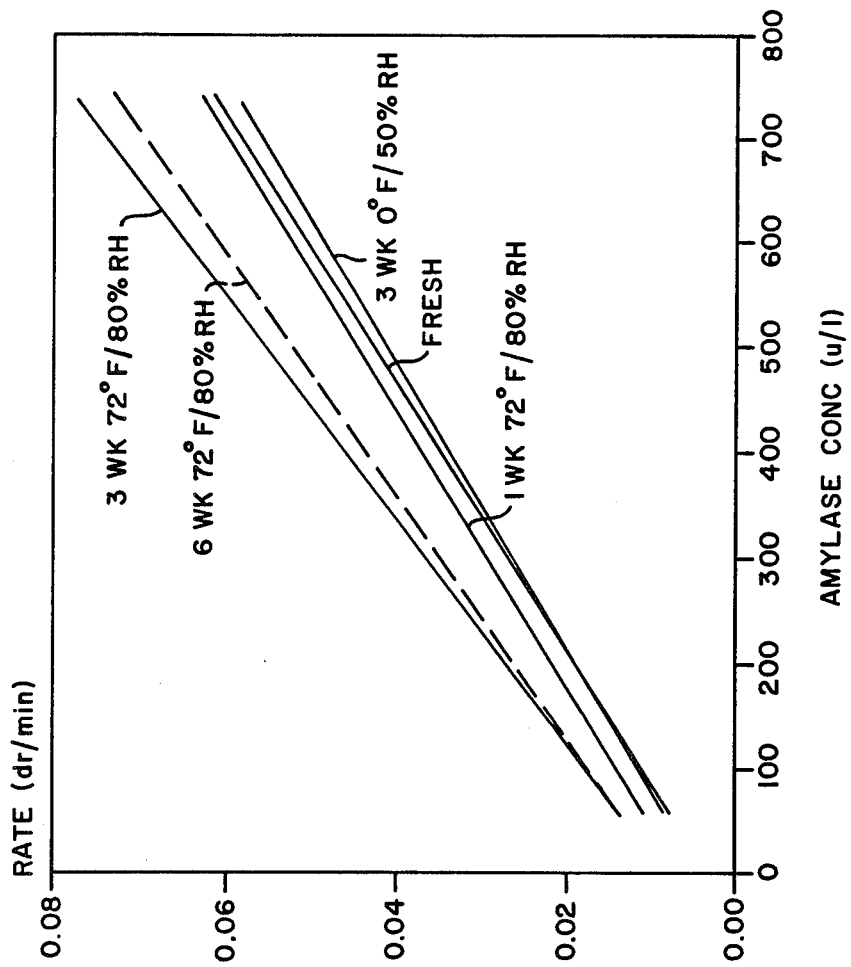
FIGS. 3 and 4 are graphs showing the reduced tendency of the elements of the invention to overpredict enzyme concentration after storage at ambient conditions.
Figure 4:
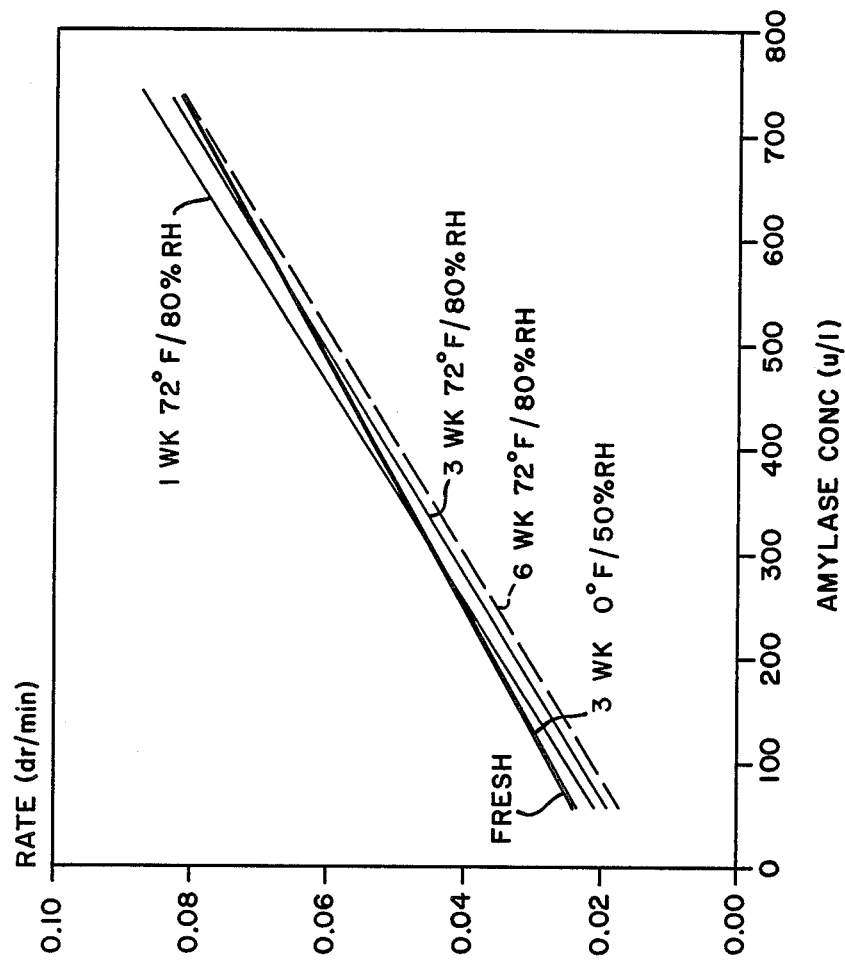
Figure 5:
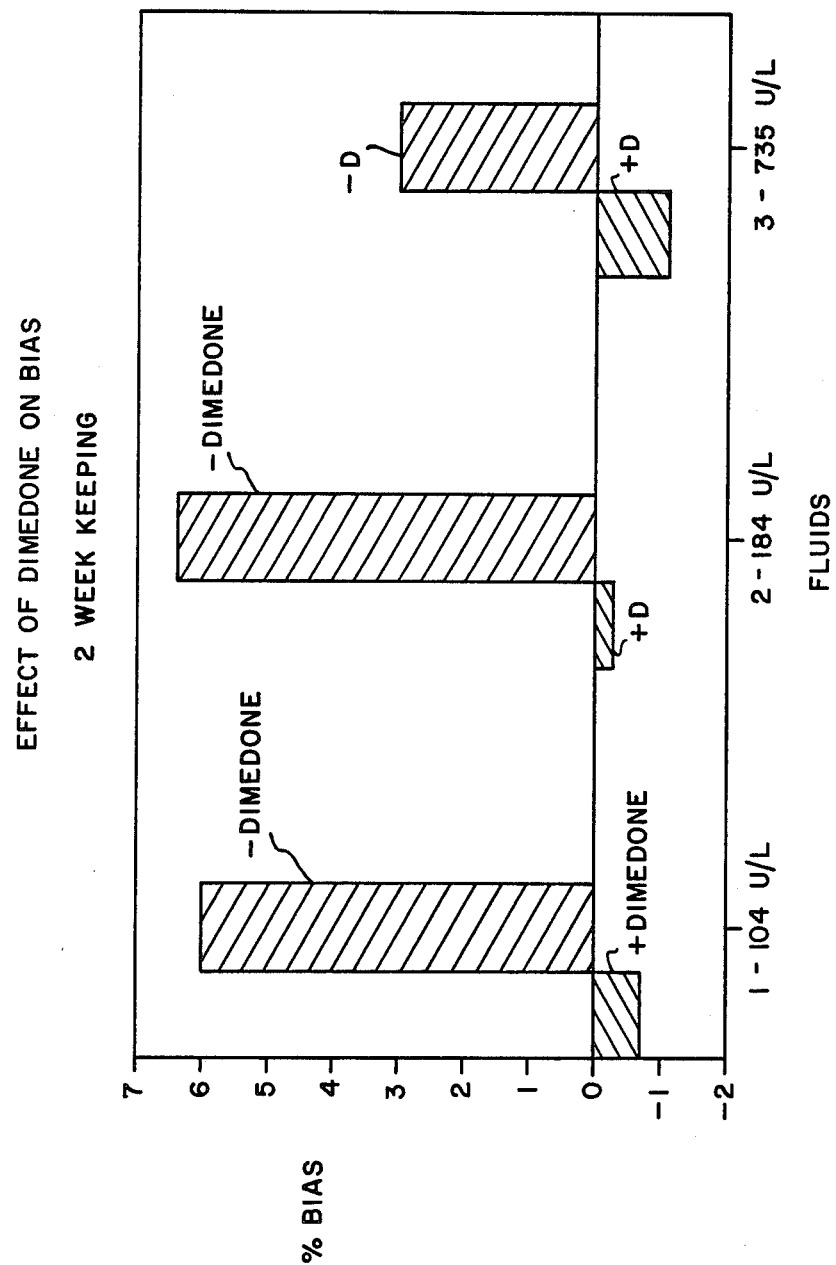
FIG. 5 is a chart representing the reduced tendency of an element of the invention to overpredict enzyme concentration.

Samples of both element formulations (with and without dimedone) are aged for various periods of time at various conditions (1 week at 72° F./80% relative humidity (RH), 3 weeks at 72° F./80% RH, 3 weeks at 0° F./50% RH, and 6 weeks at 72° F./80% RH). The aged elements and fresh elements are tested using serum based control solutions having known amylase concentrations. The results of this comparative test are shown in FIGS. 3 and 4. FIG. 3 represents the results for the element outside the scope of the invention without dimedone and FIG. 4 represents the results for the element of the invention with dimedone. The graphs of FIGS. 3 and 4 show the rate of dye released in the registration layer as a function of the actual concentration of amylase in the test liquid for: fresh elements, elements aged 1 week at 72° F./80% RH, elements aged 3 weeks at 72° F./80% RH, elements aged 3 weeks at 0° F./50% RH, and elements aged 6 weeks at 72° F./80% RH. As shown in FIG. 3, the elements outside the scope of the invention containing no dimedone show a significantly greater tendency to overpredict the concentration of amylase after aging at 72° F./80% RH than do the elements of the invention in FIG. 4. The improved performance of the elements of the invention is also shown in FIG. 5. FIG. 5 is a bar chart showing the % bias the percent by which the element over- or underpredicts the actual concentration of amylase) for amylase concentrations of 104, 184, and 735 U/L. FIG. 5 shows that elements of the invention (those containing dimedone) show a significantly reduced tendency to overpredict the concentration of amylase in the sample.

EXAMPLES 2-5

Elements according to the invention are prepared as in Example 1 using the components shown in Table 1 in place of dimedone:

TABLE 1

| Example | Component |
| --- | --- |
| 2 | dimedone (this element is essentially identical to Example 1) |
| 3 | 1-benzoylacetone |
| 4 | 1-phenyl-2,4-pentanedione |
| 5 | 1-(2-furyl)-1,3-butanedione |

The elements along with a control containing no dione in the reagent layer are kept for 16 days at 72° F./80% RH and tested with solutions of amylase at concentrations of 44 and 746 U/L. The % bias (as defined in Example 1) for each of the elements is shown in Table 2.

TABLE 2

| Example | % Bias at 44 U/L | % Bias at 746 U/L |
| --- | --- | --- |
| Control | 164 | 3.9 |
| 2 | −2 | −1 |
| 3 | −0.5 | −6 |
| 4 | −8 | −2.4 |
| 5 | 11.7 | −0.6 |

The results shown in Table 2 indicate a much lower tendency to overpredict the concentration of amylase with elements of the invention than with the control element outside the scope of the invention.

The invention has been described in detail with particular reference to preferred embodiments thereof, but it will be understood that variations and modifications can be effected within the spirit and scope of the invention.

What is claimed is:

1. A composition comprising a polysaccharide having a detectable material attached thereto and a 1,3-dione having a Pka up to 9 and methylene group between the two carbonyls of said 1,3-dione, which methylene group comprises at least one ionizable hydrogen.

2. The composition of claim 1 wherein said 1,3-dione has the structure:

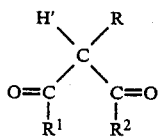

where H' is ionizable hydrogen, R is H, alkyl, aryl, or —CO—$R^3$, $R_1$ and $R^2$ each represent independently H, alkyl, aryl, —$OR^4$, a heterocyclic ring, or together represent the atoms necessary to complete a 5- or 6-membered carbocyclic ring, $R^3$ is H, alkyl, or aryl, and $R^4$ is alkyl or aryl.

3. The composition of claim 1 wherein said 1,3-dione is a beta-diketone.

4. The composition of claim 1 wherein said 1,3-dione is dimedone.

5. The composition of claim 1 wherein said 1,3-dione is a carbocyclic 1,3-dione.

6. The composition of claim 1 wherein said polysaccharide is a starch and said detectable material is a dye.

7. The composition of claim 6 further comprising a binder, an inert particulate material, and a buffer, wherein said starch, 1,3-dione, inert particulate material, and buffer are uniformly dispersed in said binder.

8. A test element for analysis of a hydrolyzing enzyme in a liquid, comprising a support having thereon:
a reagent zone including a non-diffusible polysaccharide having a detectable material appended thereto and a 1,3-dione having a methylene group between the two carbonyls of said 1,3-dione, which methylene group comprises at least one ionizable hydrogen, said non-diffusible polysaccharide being interactive in the presence of said hydrolyzing enzyme to provide a diffusible material comprising said detectable material, and
a registration zone adapted to receive said diffusible material.

9. The test element of claim 8 wherein said 1,3-dione has the structure:

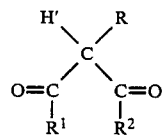

where H' is ionizable hydrogen, R is H, alkyl, aryl, or —CO—$R^3$, $R_1$ and $R^2$ each represent independently H, alkyl, aryl, —$OR^4$, a heterocyclic ring, or together represent the atoms necessary to complete a 5- or 6-membered carbocyclic ring, $R^3$ is H, alkyl, or aryl, and $R^4$ is alkyl or aryl.

10. The test element of claim 9 wherein said 1,3-dione is dimedone.

11. The test element of claim 8 wherein said non-diffusible polysaccharide is a starch, said diffusible material is a polysaccharide having a molecular weight low enough to render it diffusible, and said detectable material is a dye, and wherein the registration zone comprises a buffer and a mordant for said dye.

12. The test element of claim 8 wherein the reagent zone further comprises a binder and an inert particulate material, and wherein said 1,3-dione, non-diffusible polysaccharide, and inert particulate material are uniformly dispersed in said binder.

13. The test element of claim 8 wherein said non-diffusible polysaccharide is a starch, said diffusible material is a polysaccharide having a molecular weight low enough to render it diffusible, and said detectable material is a dye, and wherein the registration zone comprises a mordant for said dye, said test element further comprising a buffer zone between said reagent zone and said registration zone.

14. A test element for the analysis of amylase in a liquid, comprising a support having thereon:
a reagent zone including, uniformly dispersed in a binder, a non-diffusible polysaccharide having a dye appended thereto, dimedone, and an inert particulate material, said non-diffusible starch being interactive in the presence of amylase to provide a polysaccharide having a molecular weight low enough to render it diffusible, and a registration zone comprising a mordant for said dye.

15. The element of claim 14 further comprising a buffer zone between said reagent zone and said registration zone.

16. The element of claim 14 wherein said registration zone comprises a buffer.

17. The element of claim 14 wherein said particulate material is barium sulfate or titanium dioxide.

18. A method for detecting a hydrolyzing enzyme in a liquid, comprising the steps of:
 (a) contacting the liquid with the reagent zone of the test element of claim 8, so as to cause diffusion of said diffusible material to the registration zone, and
 (b) detecting the amount of said hydrolyzing enzyme in the sample as a function of the amount of said detectable material in the registration zone.

19. The method of claim 18 wherein said hydrolyzing emzyme is amylase.

* * * * *

UNITED STATES PATENT OFFICE
CERTIFICATE OF CORRECTION

PATENT NO. : 4,782,018  Page 1 of 2
DATED : November 1, 1988
INVENTOR(S) : Jon N. Eikenberry et al.

It is certified that error appears in the above-identified patent and that said Letters Patent are hereby corrected as shown below:

Col. 9, line 52, the part reading

"material attached"

should read

-- material chemically attached --;

Col. 9, line 53, the part reading

"and methylene group"

should read

-- and a methylene --;

Col. 10, line 18, the part reading

"material appended"

should read

-- material chemically attached --;

UNITED STATES PATENT OFFICE
CERTIFICATE OF CORRECTION

PATENT NO. : 4,782,018
DATED : November 1, 1988
INVENTOR(S) : Jon N. Eikenberry et al.

It is certified that error appears in the above-identified patent and that said Letters Patent are hereby corrected as shown below:

Col. 10, line 19, the part reading

"having a methylene"

should read

-- having a Pka up to 9 and a methylene --; and

Col. 11, line 1, the part reading

"dye appended"

should read

-- dye chemically attached --.

Signed and Sealed this

Fourth Day of April, 1989

Attest:

DONALD J. QUIGG

Attesting Officer

Commissioner of Patents and Trademarks